United States Patent
Freeouf (10) Patent No.: US 6,323,947 B1
(45) Date of Patent: Nov. 27, 2001

(54) ANGLE OF INCIDENCE ACCURACY IN ULTRATHIN DIELECTRIC LAYER ELLIPSOMETRY MEASUREMENT

(75) Inventor: John Lawrence Freeouf, Katonah, NY (US)

(73) Assignee: Interface Studies Corporation, Katonah, NY (US)

( * ) Notice: Subject to any disclaimer, the term of this patent is extended or adjusted under 35 U.S.C. 154(b) by 0 days.

(21) Appl. No.: 09/461,658

(22) Filed: Dec. 14, 1999

(51) Int. Cl.$^7$ ........................................ G01J 4/00
(52) U.S. Cl. .................. 356/369; 356/365; 356/366; 356/367; 250/225
(58) Field of Search ...................... 356/365, 366, 356/367, 368, 369; 250/225

(56) References Cited

U.S. PATENT DOCUMENTS

| | | | |
|---|---|---|---|
| 3,880,524 | 4/1975 | Dill et al. | 356/118 |
| 4,053,232 | 10/1977 | Dill et al. | 356/118 |
| 4,332,833 | 6/1982 | Aspnes et al. | 427/8 |
| 4,653,924 | 3/1987 | Itonaga et al. | 356/369 |
| 4,672,196 | 6/1987 | Canino | 250/225 |
| 4,762,414 | 8/1988 | Grego | 356/349 |
| 4,837,603 | * 6/1989 | Hayashi | 456/369 |
| 5,091,320 | 2/1992 | Aspnes et al. | 437/8 |
| 5,277,747 | 1/1994 | Aspnes et al. | 156/626 |
| 5,526,117 | 6/1996 | Wielisch et al. | 356/369 |
| 5,595,916 | 1/1997 | Fujimura et al. | 437/8 |
| 5,608,526 | 3/1997 | Piwonma-Corle et al. | 356/369 |
| 6,222,199 | 4/2001 | Freeouf | 250/559.27 |

FOREIGN PATENT DOCUMENTS

| | | |
|---|---|---|
| 63-12906 | 1/1988 | (JP) . |
| 6423105 | 1/1989 | (JP) . |
| 5-263244 | 10/1993 | (JP) . |

OTHER PUBLICATIONS

R. L. Johnson et al, "Spectroscopic Ellipsometry With Synchrotron Radiation", Review of Scientific Inst. vol. 60(7) Jul. 1989 pp. 2209–2212.

(List continued on next page.)

*Primary Examiner*—Hoa Q. Pham
*Assistant Examiner*—Sang Hoang Nguyen (57) ABSTRACT

Improvements in accuracy and sensitivity in mechanical-optical metrology apparatus are achieved through the use of a value for angle of incidence that is an average of positive and negative values for different arrangements of the metrology apparatus. In the ellipsometry type of metrology the average value for angle of incidence is established by using one of a reversal of light beam direction, the providing of a separate light beam mounting arm and the mechanical rotation of the sample.

12 Claims, 6 Drawing Sheets

OTHER PUBLICATIONS

Germer Et Al, "Plarization of Out–of–Plane Scattering from Microrough Silicon", Optics Letters, vol. 22 (17) Sep. 1997 pp. 1284–1286.

P.S. Hauge, "Recent Developments in Instrumentation in Ellipsometry," Surface Science, vol. 96, No. 1–3, 1980, pp. 108–140.

Henneth K. Ellis, "Polarimetric Bidirectional Reflectance Distribution Function of Glossy Coatings", J. Opt. Soc. Am., vol. 13, No. 8, Aug. 1996 pp. 1758–1762.

Deumié Et Al, "Ellipsometry of Light Scattering from Multilayer Coatings", Applied Optics, vol. 35 No. 28, Oct. 96, pp. 5600–5608.

U. Rossow Et Al, Interpretation of Surface–Induced Optical Anisotropy of Clean, Hydrogenated, and Oxiidized Vional Silicon, Surfaces Investigated by Reflectance Difference Spectroscopy, J. Vac. Sci. Tech. B, 14, 4, Jul./Aug. 1996 pp. 3070–3074.

John L.Freeouf, "Application of Spectroscopic Ellipsometry to Complex Samples", App. Phys. Ltrs. 53,(24), Dec. 88 pp. 2426–2428.

D.E. Aspnes, Analysis of Semiconductor Materials and Structures by Spectroellipsometry S.P.I.E. vol. 946, 1988 pp. 84–97.

Sales Brochure, J.A.Woolam Co., Variable Angle Spectroscopic Ellipsometers, 8 pages.

Sales Brochure, "Infrared Spectroscopic Ellipsometer SE900", Sentech, Instruments, 4 pages.

T.E Faber and N.V. Smith, "Optical Measurements on Liquid Metals Using a New Ellipsometer" Journal of the Optical Society of America, vol. 58, No. 1, Jan. 1968, pp. 102–108.

Bertucci Et Al, "Systematic Errors in Fixed Polarizer, Rotating Polarizer, Sample, Fixed Analyzer, Spectroscopic Ellipsometry," Thin Solid Films 313–314 (1998) 73–78.

Azzam et al, "Analysis of Systematic Errors in Rotating–Analyzer Ellipsometer"Journal of the Optical Society of America, vol. 64, No. 11, Nov. 1974, pp. 1459–1469.

* cited by examiner

ANGLE OF INCIDENCE ACCURACY IN ULTRATHIN DIELECTRIC LAYER ELLIPSOMETRY MEASUREMENT

CROSS REFERENCE TO COPENDING APPLICATIONS

Cross Reference is made to U.S. patent application Ser. No. 09/160,017, Filed Sep. 24, 1998, of John L. Freeouf, titled HIGH PHOTON ENERGY RANGE REFLECTED LIGHT CHARACTERIZATION OF SOLIDS, assigned to the assignee of the application, and to U.S. patent application Ser. No. 09/318,035 filed May 25, 1999 of John L. Freeouf, titled MEASUREMENT OF THE ULTRATHIN DIELECTRIC LAYERS assigned to the assignee of this application, both arising out of continuing effort by the assignee of this application and both incorporated herein by reference.

FIELD OF THE INVENTION

The invention relates to the use of averaging of + and − values of a parameter in mechanical-optical metrology apparatus to establish an assigned value for use in the apparatus in highly sensitive applications and in particular to the establishing of an averaged value of the angle of incidence of a, to be reflected light beam, in ellipsometry.

BACKGROUND OF THE INVENTION AND RELATION TO THE PRIOR ART

Ellipsometry metrology involving apparatus in which samples to be studied are mechanically positionable and changes in reflected light from the samples is used in feature identification or characterization of the surface and bulk aspects of solid materials is becoming of increasing necessity as the dimensions being studied become smaller. The terminology "sample" is used for explanation simplicity. In metrology, the apparatus and analytical principles involved are useable in single, batch and on line types of operation in arrangements where an incident beam of polarized light is reflected from a sample under study and differences in the polarization of the reflected light that are produced by the reflection from the sample provide the measured quantities. The metrology operations require tedious data taking involving calibrated interaction of mechanical and optical components. One of the most influential parameters is the angle of incidence of the beam of polarized light, when the beam reflects from the sample. Any error in the value assumed in the data taking for the angle of incidence, especially where small dimensions are involved, is frequently only identified after considerable apparatus calibration time and effort. There are needs in the ellipsometry metrology art for ways of providing accurate assumed values for all parameters and in the case of the angle of incidence the need is particularly acute.

SUMMARY OF THE INVENTION

Improvements in accuracy and sensitivity in mechanical-optical apparatus are achieved through the use of a value for angle of incidence that is an average of positive and negative values for different arrangements of the metrology apparatus. In the ellipsometry type of metrology the average value for angle of incidence is established by using one of a reversal of light beam direction, the providing of a separate light beam mounting arm and the mechanical rotation of the sample.

BRIEF DESCRIPTION OF THE DRAWINGS

FIGS. 8 and 9 are line illustrations of the relative positions of the parts of the ellipsometry apparatus where there is rotation around an axis of rotation, in which:

FIGS. 10 and 11 are graphs showing variation of Delta vs Photon Energy, in which.

DESCRIPTION OF THE INVENTION

In accordance with the invention in mechanical-optical metrology apparatus accuracy of an assigned value of a sensitive parameter can be assured by taking an average of + and − values of the parameter achieved by manipulation of the apparatus into opposite mathmatical sign regimes of the information equations.

The principle involved is a manifestation of the fact that a function F(x) can be expanded locally as a polynomial as in $$F(x) = A + Bx + Cx^2 + Dx^3 \text{ etc.} \qquad \text{(Equation 1)}$$

For sufficiently small values of x, such as is the case in ellipsometry, Equation 1 reduces to $$F(x) = A + Bx, \text{ and, for even functions } B = 0. \qquad \text{(Equation 2)}$$

When angular errors are sufficiently small, all terms but the linear term can be ignored and high accuracy can be achieved by averaging the + and − values.

In this invention use is made of this principle to improve the accuracy of optical operations in which the parameter "x" in equations 1 and 2 refers to some aspect of the angle between the incident light and the sample surface normal, and the function F(x) may be an ellipsometric parameter such as Δ or ψ, or may be some other aspect of the interaction of light with the solid, such polarization-dependent reflectance or transmission, in which the governing equations, for each interface, are the Fresnel coefficients for reflectance or transmission as needed. The Fresnel equations are indeed functions of the angle of incidence and of material properties of the sample. In equations 5 and 6 below, the ellipsometric parameters Δ and ψ are also functions of the angle of incidence and of material properties of the sample.

In the practice of ellipsometry metrology, among the errors that can have substantial impact upon the absolute accuracy and precision of the results, is the precisely defining and determining of the angle of incidence of the light with respect to the sample under study. In the art the defining and determining of the angle of incidence is done with respect to an imaginary perpendicular through the sample known in the art as the "normal", extending vertically from the surface of the sample, and around which the sample may be rotated. The angle of incidence is a crucial parameter in the ellipsometry equations. It is however also highly accuracy sensitive in that it can be affected with many types of misadjustment such as sample misalignment and drift in the optical components. At the present state of the art the adjustment and calibration for use of an ellipsometry metrology apparatus can require an extensive effort on the part of a highly skilled operator.

The invention can be understood with added clarity using, as an example, ellipsometry metrology where the sign of an error departing from a value of the angle of incidence can be inverted by a departure from the value in the opposite direction. The departure can be produced by changes in the relation between the sample under study and the incident light so as to invert the error. In practice this means that elaborate techniques to establish and maintain a value for the angle of incidence for each change of sample can be replaced by simple averaging of two values on either side of the actual value.

Figure 1:
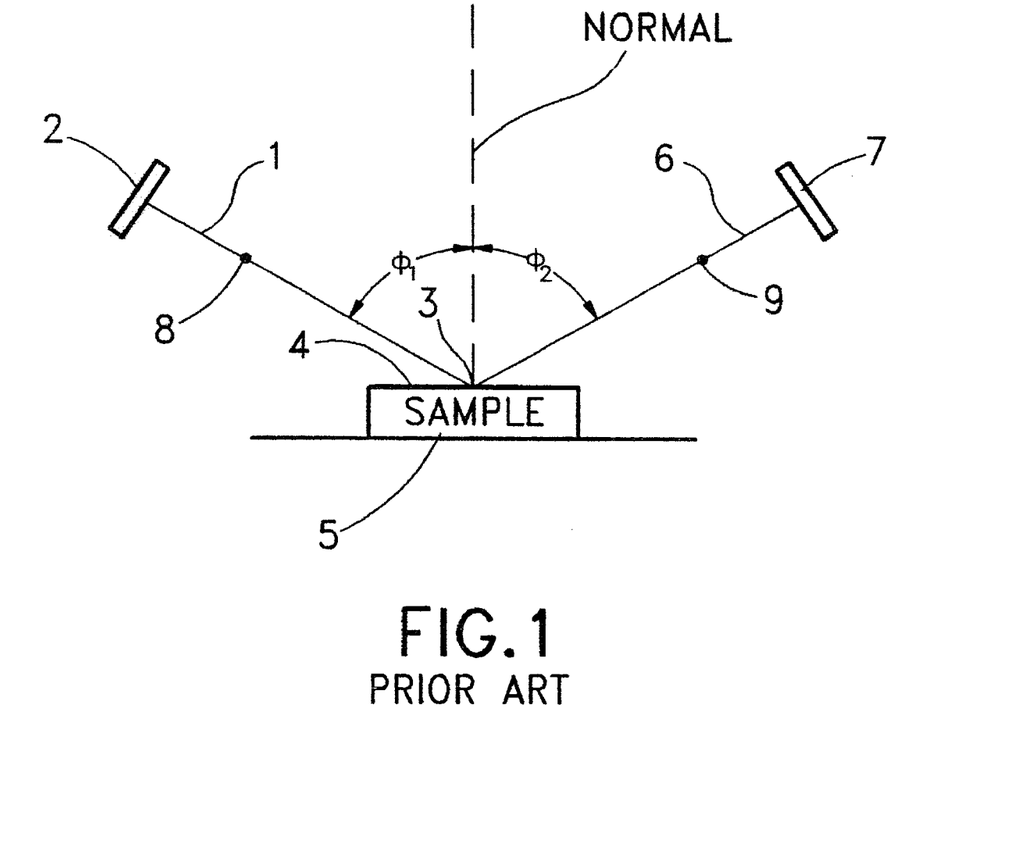
FIG. 1, labelled prior art, is a schematic illustration of the features involved in a typical ellipsometry metrology apparatus.

Referring to FIG. 1, labelled prior art, there is shown a schematic illustration of the features involved in a typical ellipsometry metrology apparatus. In FIG. 1 incident light from a light source is reflected from the surface of a sample of a material under study and changes are detected that indicate differences in the properties of the sample. In the specific apparatus of FIG. 1, incident light 1, from a light source 2, is reflected at 3 from the surface 4 of a sample 5 of a solid material under study. The reflected light 6 from the sample 5 is sensed in a detector 7. In some constructions the incident light beam 1 receives an initial polarization at 8 and changes in that polarization are analyzed in the reflected beam 6, at 9. The detector 7 receives the output signal of the analysis at 9. The angle of incidence between the incident light beam 1 and the normal is labelled $\phi_1$. In many constructions the angle of reflection $\phi_2$ between the normal and the reflected light beam 6 is equal to $\phi_1$. It is necessary only that all the light in beam 6 reach the detector $7_1$, except for losses due to detection of polarization state, which is done by rejecting light having an orthogonal polarization state.

In ellipsometry metrology the information about the sample 5 is achieved using two parameters that are responsive to the reflection from the sample. The parameters are: the change in ratio of reflected intensity in two orthogonal directions, known in the art as TanPsi (ψ), and the change in the phase difference between two different polarization states, known in the art as CosDelta (Δ).

The following sample equations 5 and 6 are employed in the analysis of the detected information in FIG. 1 for the case of a bare substrate. The equations are types standard in the art such as those reported by T. E. Faber and N. V. Smith in the Journal of the Optical Society of America, 58, 102, (1968).

$$\epsilon_1 = Sin^2\phi Tan^2\phi \frac{(Cos^2 2\psi - Sin^2 2\psi Sin^2\Delta)}{(1 + Cos\Delta Sin 2\psi)^2} + Sin^2\phi \qquad Eq. 5$$

$$\epsilon_2 = \frac{Sin 2\psi Cos 2\psi Sin\Delta}{2Sin^2\phi Tan^2\phi(1 + Cos\Delta Sin 2\psi)^2} \qquad Eq. 6$$

Where $\epsilon_1$ and $\epsilon_2$ are real and imaginary dielectric functions at that photon energy and the angle of incidence is φ.

Figure 2:
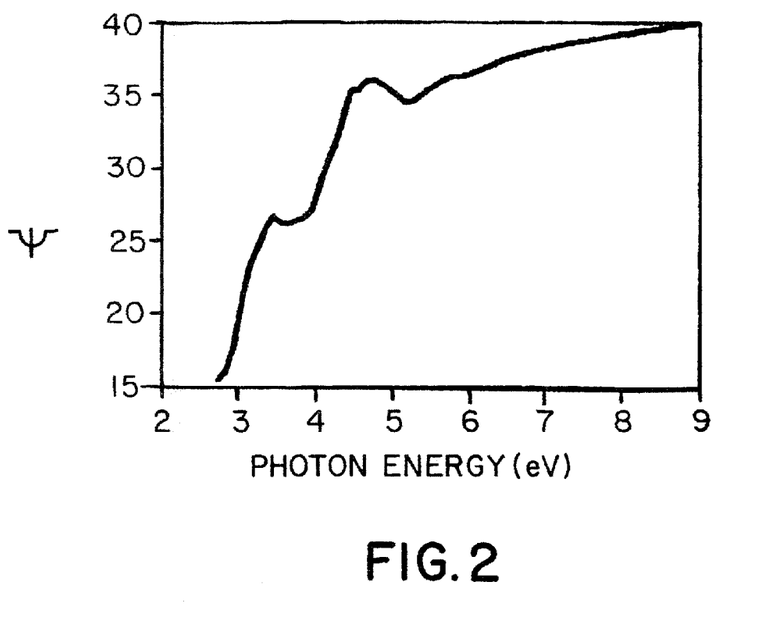
FIGS. 2 and 3 are illustrative graphs of the variation of the (Psi ψ) and (Delta Δ) parameters employed in ellipsometry metrology, with variation of photon energy, for an example 70 degree angle of incidence on an example three layer oxide on nitride on oxide on silicon substrate, where the total combined layer is less than ten nanometers thick as would occur in an apparatus such as FIG. 1.
Figure 3:
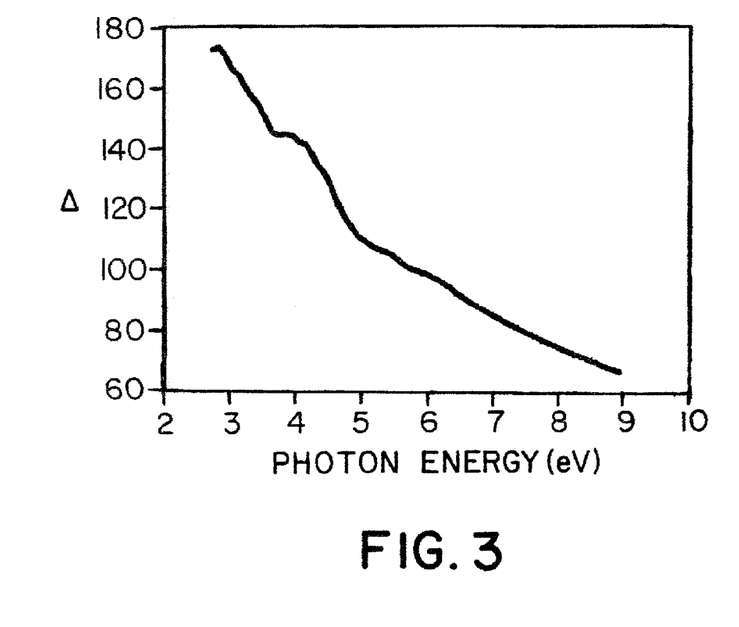

The values acquired for Psi (ψ) and Delta (Δ) vary over the entire range as is indicated by the two examples in FIGS. 2 and 3 for the incident light beam photon energy parameter. The examples are of the variation of the parameter at an angle of incidence of 70 degrees reflected from a three layered sample of oxide on nitride on oxide on a substrate where the three layer sample has a combined thickness of about 10 nanometers. Such a set of conditions is typical of the gate of a semiconductor field effect transistor.

In the information collection and analysis in the practice of ellipsometry, a large number of data points are assembled. It will be apparent that the accuracy, maintainability and reproducibility of the value of the angle of incidence is essential to efficiency and accuracy in ellipsometry metrology.

In accordance with the invention an assumed value for the angle of incidence can be rendered highly accurate with the simple expedient of taking a reading in a region where the sign is opposite and averaging the values.

As may be seen from the above equations 5 and 6 the angle of incidence is so thoroughly involved, that the ability to precisely define and determine that angle in accordance with this invention will have a substantial impact on the accuracy and precision of ellipsometry measurements.

Figure 4:
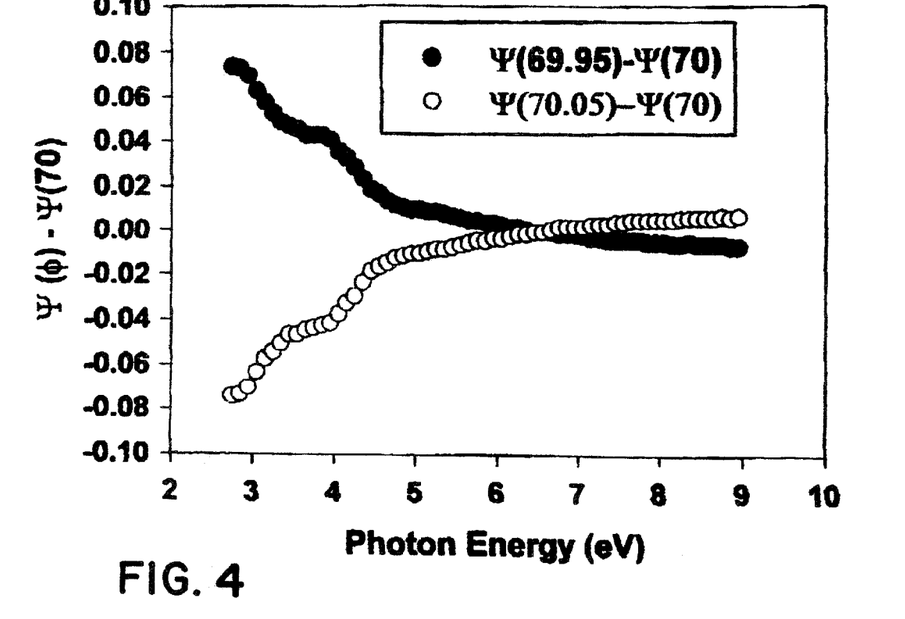
FIGS. 4 and 5 respectively are graphs of the effects of positive and negative angle of incidence errors on the (Psi ψ) and (Delta Δ) parameters employed in ellipsometry metrology, with variation of photon energy, as would occur in an apparatus such as FIG. 1.
Figure 5:
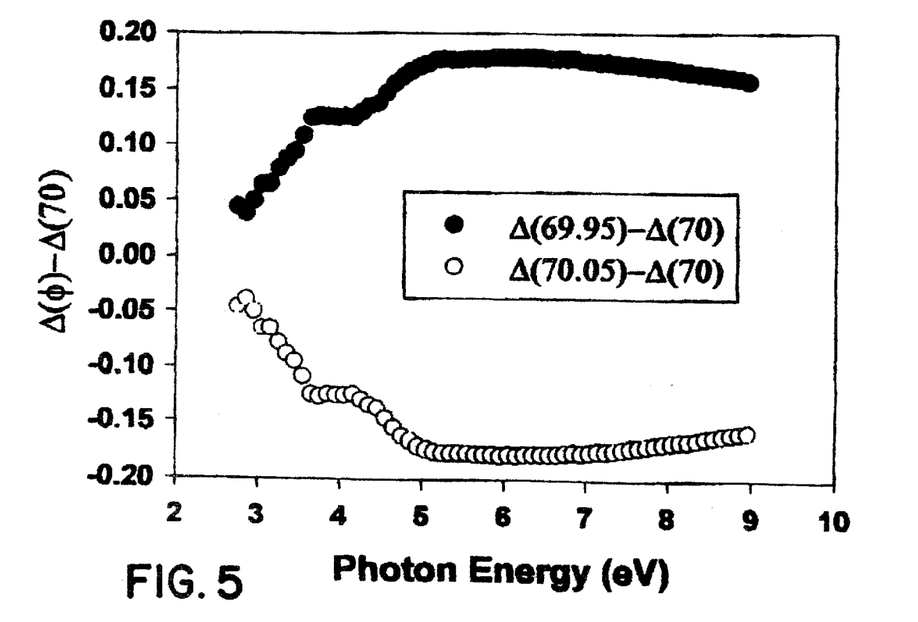

As an example of the impact of errors in the angle of incidence parameter. FIGS. 4 and 5 are provided, which are calculations of an 0.05 degree variation on either side of a 70 degree angle of incidence, for the Psi (ψ) and Delta (Δ) respectively. The impact of the 0.05 variations may be seen in the following ellipsometric exercise to identify the best dielectric parameters for a dielectric stack that will become a semiconductor device gate. The data in table 1 is the ellipsometric response of a 6 Å Oxide upon 4 Å Nitride upon 6 Å Oxide on a Silicon substrate at 70 degrees, 70.05 degrees and a 69.95 degrees. The calculation is the total thickness of the oxide as well as the nitride thickness. There is a standard in the ellipsometric art "goodness of fit" (χ), of the data, and, in accordance with the invention, the average of the + and −0.05 degree variations is tabulated.

TABLE 1

| True Angle Degrees | Nitride thickness Angstroms | Oxide thickness Angstroms | Goodness of fit $\chi^2$ |
|---|---|---|---|
| 70 | 4.0000 A° | 5.9997 A° | 0.0000346 |
| 70.05 | 4.1 A° | 6.3 A° | 0.3 |
| 69.95 | 3.9 A° | 5.68 A° | 0.3 |
| Average of 70.05 and 69.95 | 3.9998 | 6.0008 | 0.000019 |

In accordance with the invention the angle of incidence errors almost totally cancel each other. The cancellation is shown in graphical form for Psi (ψ) in FIG. 4 and for Delta (Δ) in FIG. 5. On either side of 70 the difference has comparable magnitude but opposite sign providing the error cancellation.

In practice this means that elaborate techniques such as are currently practiced in the art to establish angle of incidence to high precision become much simpler with this invention in which there is a first estimate of the angle followed by a change in the relation between the sample and the incident light so as to invert the error and the error on each side averages out. The advantages of the invention become clearer using as an example the 0.05 degree type departure such as in Table 1 and FIGS. 4 & 5 and the commonly used angle of incidence value of 70 degrees from the sample normal which is 20 degrees from parallel to the sample surface. In this situation rotating the sample by 140 degrees, the angle of incidence will again be 70 degrees. If the first 70 degree angle had a slightly under, 0.05 degree departure from precisely 70 degrees, in other words 69.95 degrees, then the second angle, after the 140 degree rotation, will be slightly over 70 degrees by the same amount which is 70.05 degrees. This will be true within the mechanical limits of the sample rotation.

Thus, what has been accomplished is that the ability to define the value of the angle of incidence has been reduced from a surveying like problem in precisely delineating the intensity distribution at all wavelengths from a light source that may not be as collimated or point source like as is a laser, to an infinitely simpler procedure where the precise angle is approximated, measurements taken at each limit of a precise rotation and the values averaged as shown in Table 1. The mechanical rotation can be accomplished to great accuracy by adding to the type of apparatus of FIG. 1, a high precision absolute optical encoder, an inductosyn encoder, or other means of being able to control rotation within about 0.001 degree, and used simply to calibrate a two position rotor. This also permits movement to another ellipsometer apparatus. The technique of this invention may be contrasted with the standard approaches in the art for establishing an angle of incidence value which are normal surveying and light deflection techniques and the measuring of one or more reference samples and then find the angle of incidence value that provides the best "least squares" type fit to the expected sample structure. The averaging technique of this invention offers the possibility of much greater accuracy as may be seen from the "Average" row of Table 1. The proper ellipsometric parameters for the presumed angle of incidence are recovered from two measurements neither one of which was performed at the correct angle of incidence.

The difference between the measured value (at the incorrect angle) and the averaged (which is the correct angle data) is useable to determine the true angle at which the measurement was performed. Such information is also useful in minimizing repetitive measurements on like samples.

In ellipsometry metrology apparatus the light and mechanical componentry can both be used in adjusting the apparatus to positions where the sign of an error departing from a value of the angle of incidence can be inverted by a departure from the value in the opposite direction.

Figure 6:
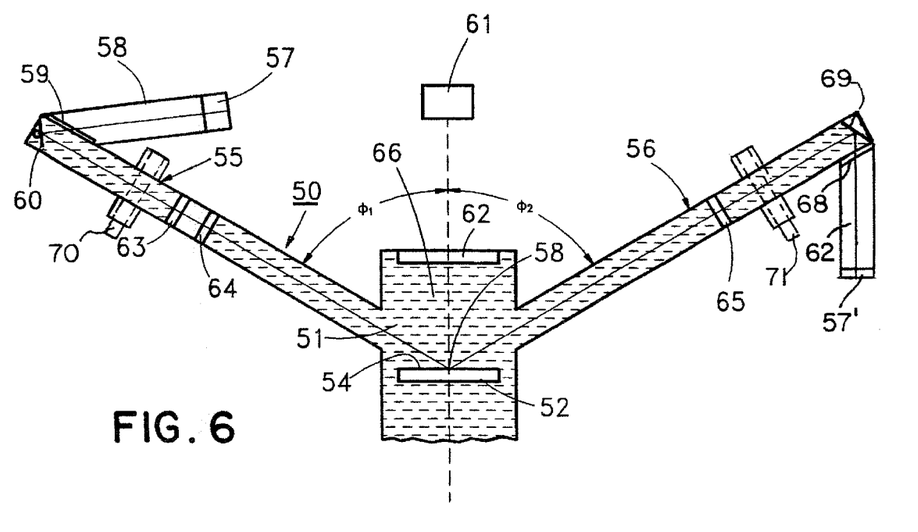
FIG. 6 is an ellipsometry apparatus employing the invention with a light source in each of the incident and the detection arms.
Figure 7:
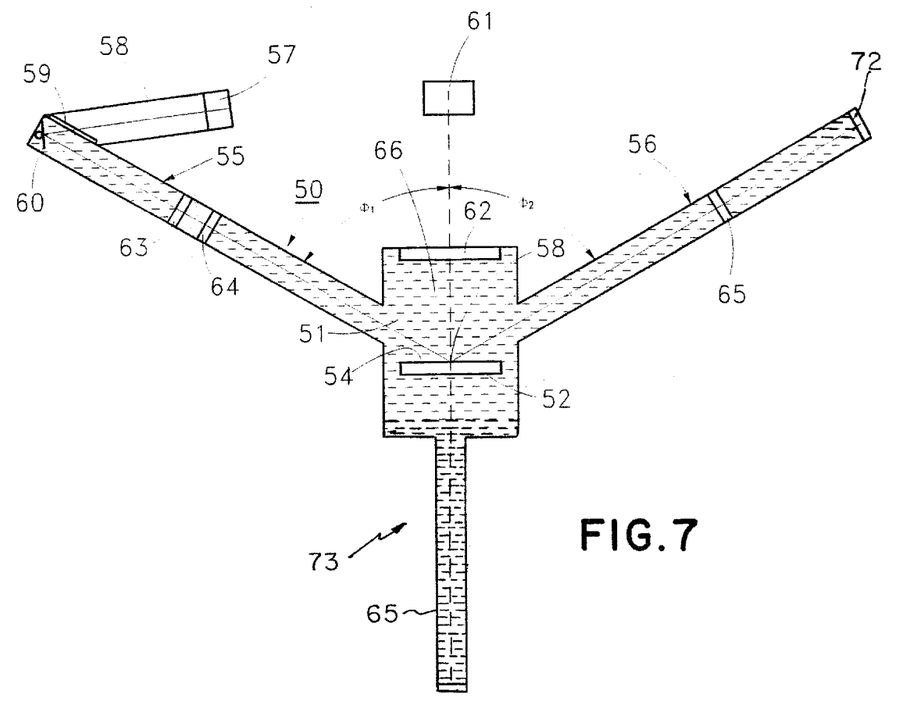
FIG. 7 is an ellipsometer apparatus employing the invention with a separate light source located in a separate arm.

In FIGS. 6 and 7 illustrations are provided of illustrative arrangements in which the relationship between the mechanical and the light portions of the system is altered sufficiently to produce averagable measurements with different signs.

Referring to FIG. 6 there is shown a BiDirectional Ellipsometry type of metrology apparatus equipped, in accordance with the invention with the ability to direct the light in two directions through the apparatus, whereby achieving angle of incidence values with different signs. In the apparatus of FIG. 6 a special ambient 66 is provided throughout the light path from the light source to the detector. The special ambient is achieved by providing a housing 50 surrounding a vacuum or inert gas ambient. The housing 50 has a central section 51 in which the sample 52 with the reflection at 53 off the surface 54 are located. The housing 50 further has an arm 55 for the incident light and an arm 56 for the reflected light portion of the light path. The angle of incidence is labelled $\phi_1$ and the angle of reflection is labelled $\phi_2$. The light source is labelled 57 and is positioned on a branch 58 of the arm 55 with an isolating window 59 that passes, essentially unattenuated, the light from the source 57 while permitting the branch 58 to have a different controlled ambient, if desired. The light from the light source 57 enters the arm 55 and is reflected from an adjustable mirror 60 which facilitates focusing of the light path in the housing 50 to the reflection location 53 on the surface 54 of the sample 52. The alignment of the sample 52 is facilitated through the use of a standard autocollimator 61 and glass window 62. The positioning of the sample 52 and alignment of the reflected light portion of the light path is facilitated using a goniometer, not shown, on which the sample may be mounted. The polarization of the incident light in the light path is provided through a fixed polarizer 63 and rotating polarizer 64 assembly and the measurement of the elliptical polarization of the reflected portion of the light path is provided with polarizer 65.

In accordance with the invention, the apparatus of FIG. 6 thus far, can be modified to provide a capability of taking a second angle of incidence measurement that will carry a different sign and thus provide an averageable value by:

constructing the position of arm 56 so that the angle of incidence $\phi_1$ is equal to the angle of reflection $\phi_2$;

providing an assembly of elements 57,67,68 and 69 positioned at the end of arm 56, that is comparable structurally and functionally to the assembly of elements 57,58,59 and 60 positioned at the end of arm 55; and, providing identical, removable, standard in the art type, detectors 70 and 71, in arms 55 and 56 respectively.

The result of the modifications, in accordance with the invention, is that the angle of incidence value for $\phi_1$ in equations 5 and 6 can now be achieved by measurement of the light from source 57 at detector 71 and measurement of the light from source 57 at detector 70 which when averaged provide much greater accuracy and simplification than has been achieved heretofore in the art.

In view of the above it will thus be apparent that in an ellipsometer that has an incidence and a reflection arm if one simply mounts a light source on both arms and fixes the optics such that the angular relationship between the two beams is well defined and a capability to measure the light from one beam in the other; the average angle of incidence is then exactly one half the angular difference between the two arms. Where the two arms are 140 degrees apart, the angle of incidence value would be half, or 70 degrees. This approach requires that the incident beam angle $\phi_1$, be fixed to high precision but it accepts that the detected beam angle $\phi_2$ can be a less well defined value.

In FIG. 7 a further illustration is provided of the arrangement of the light for the averaging measurements. In FIG. 7 a two arm ellipsometric metrology apparatus is modified with a separate reflection arm and the capability of angular rotation of the sample for angle of incidence averaging in accordance with the invention.

Referring to FIG. 7, using the same reference numerals as in FIG. 6 where appropriate, there is shown a BiDirectional Ellipsometry type of apparatus, equipped in accordance with the invention with a capability to reflect light from two locations in the apparatus, whereby achieving angle of incidence values with different signs.

In the apparatus of FIG. 7 a special ambient is provided throughout the light path from the light source to the detector. The special ambient is achieved by providing a housing 50 surrounding a vacuum or inert gas ambient. The housing 50 has a central section 51 in which the sample 52 with the reflection at 53 off the surface 54 are located. The housing 50 further has an arm 55 for the incident light and an arm 56 for the reflected light portion of the light path. The angle of incidence is labelled $\phi_1$ and the angle of reflection is labelled $\phi_2$. The light source is labelled 57 and is positioned on a branch 58 of the arm 55 with an isolating window 59 that passes, essentially unattenuated, the light from the source 57 while permitting the branch 58 to have a different controlled ambient, if desired. The light from the light source 57 enters the arm 55 and is reflected from an adjustable mirror 60 which facilitates focusing of the light path in the housing 50 to the reflection location 53 on the surface 54 of the sample 52. The alignment of the sample 52 is facilitated through the use of a standard autocollimator 61 and glass window 62. The positioning of the sample 52 and alignment of the reflected light portion of the light path is facilitated using a goniometer, not shown, on which the sample may be mounted. The polarization of the incident light in the light path is provided through a fixed polarizer 63 and rotating poarizer 64 assembly and the measurement of the elliptical polarization of the reflected portion of the light path is provided with polarizer 65. The differences in polarization are detected in detector 72.

In accordance with the invention, the apparatus of FIG. 7 thus far, can be modified to provide a capability of taking a second angle of incidence measurement that will carry a different sign and thus provide an averageable value by:

constructing a separate arm 73, aligned with the normal of the sample 52 and having a detector 65; and, providing a capability for rotating the sample with the normal as the axis so as to establish an angle of reflection from the sample 52 that coincides with the extended normal in the arm 73. The normal is shown as a dotted line through the reflection location 53 and through the longitudinal center of arm 73.

The result of the modifications to FIG. 7, in accordance with the invention, is that the angle of incidence value for $\phi_1$ in equations 5 and 6 can now be an average measurement with much greater accuracy and simplification than has been achieved heretofore in the art.

In view of the above it will thus be apparent that in an ellipsometer, the construction of a second reflection arm along the extended normal, accompanied by a capability to align the reflected light along that second reflection arm will permit the + and − measurements for angle of incidence averaging.

The concept of averaging of values measured at two different angles may be applied to the apparatus as well as the light. There are situations where some light sources exhibit effective positions depending on wavelength and in situ studies of samples may be useful inside a separate chamber. In such situations there is not much flexibility to modify the ellipsometer, but in accordance with the invention, the + and − measurements for accuracy through averaging may also be achieved by rotation of, either the sample or the ellipsometer apparatus with respect to an axis of rotation and with the relation of the sample normal to the light source providing the measurement location. It is only required that the angle of incidence of the ellipsmeter be well defined with respect to an axis of rotation, and that the axis of rotation while it may be that of the apparatus or the sample, it must be approximated the same as the sample normal. It is the difference between the axis of rotation and the sample normal that leads to an angle of incidence error.

Figure 8:
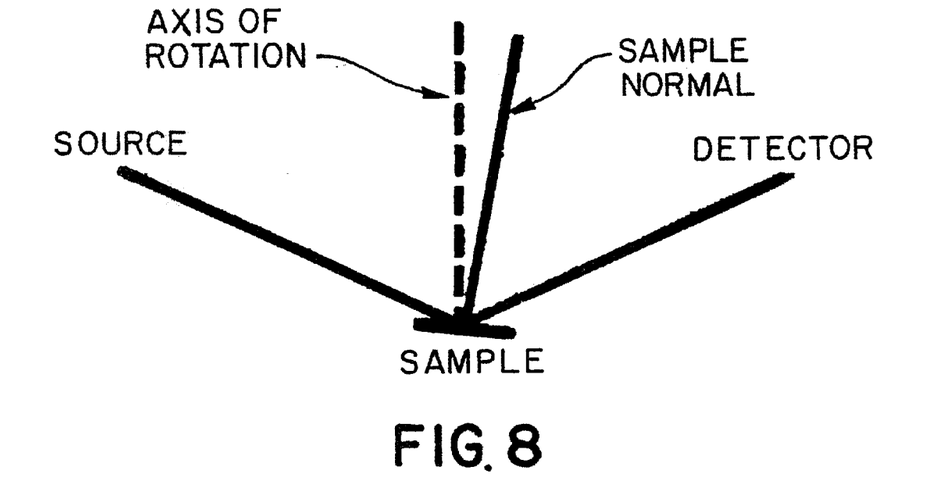
FIG. 8 is a line illustration of the principles involved where an initial measurement is made in a position where the sample normal is away from the light source; and, FIG. 9 is a line illustration of the principles involved where a second measurement is made after rotating the sample by 180 degrees; thus moving to a position where the sample normal is toward the light source.
Figure 9:
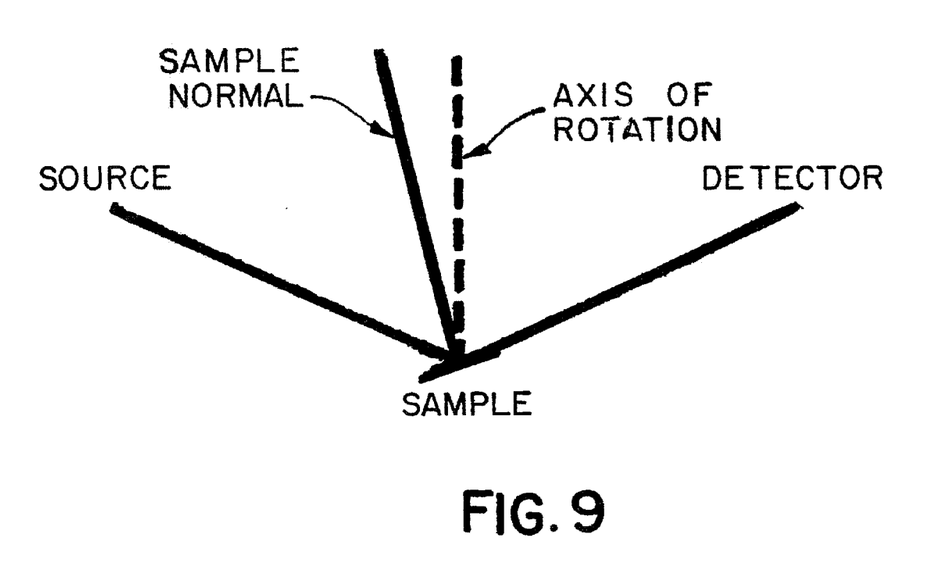

In FIGS. 8 and 9 there are shown line type illustrations of the relationship of the sample normal in relation to the source and detector locations as the sample is rotated around an axis of rotation. The illustration is for a single plane or specular situation however with additional mathematical detail the concepts may be extended to out of plane ellipsometry. In 1997 Germer et al. in an article titled "Polarization of Out of Plane Scattering of Microrough Silicon" in Optics Letters, Vol. 22, No. 17, September 1997, Pages 1284–1286 indicates the advantages of polarization information that is out of the plane of the device, i e BiDirectional Ellipsometry.

Referring to FIGS. 8 and 9 the relative positions of the sample, the light source and the detector are shown for two measurements of angle of incidence where the sample is rotated 180 degrees around the axis of rotation. The first position measurement as illustrated in FIG. 8 is taken where the sample normal difference from the axis of rotation is maximized on the side of the detector. The sample is then rotated approximately 180 degrees for a second position measurement as illustrated in FIG. 9, where the sample normal difference from the axis of rotation is maximized on the side of the light source.

In the embodiment of the invention as depicted through FIGS. 8 and 9 an additional benefit is acquired in that through the rotation of the sample errors in the plane of incidence as well as the angle of incidence may be cancelled out.

In practicing the invention there is an initial alignment of the system with the initial angle of incidence approximation close enough for the small angle approximations to be valid. The types of systems may be viewed as being of two types, those where the average angle of incidence is whatever it is, and those where the angle of incidence is defined by the sample motion. For example in the technique illustrated in connection with FIGS. 8 and 9, where the sample is rotated by 180 degrees, on an axis that is close to the sample normal, the averaging for the angle of incidence will be between the light and the axis of rotation so that in the initial alignment of the apparatus the coincidence of the rotation axis and the normal of the sample surface must be measured and established carefully. Further in practicing the invention, it should be noted that although the averaging will act on both angle of incidence and plane of incidence errors, the angular error that is acceptable may differ for the different types of errors. In the initial calibration adjustment the sample should be arranged for the first measurement so as to make the error predominantly in the direction permitting the largest error for the correction to apply; when this is done the 180 degree rotation will ensure the subsequent measurement also meets this requirement.

As an example of a system such as FIG. 6 where the sample is rotated by 140 degrees in an axis within it's surface or in other words perpendicular to the sample normal, the initial angle of incidence is set by the sample motion and must be sufficiently close to the correct angle for the small angle approximations in the equations to be valid.

Figure 10:
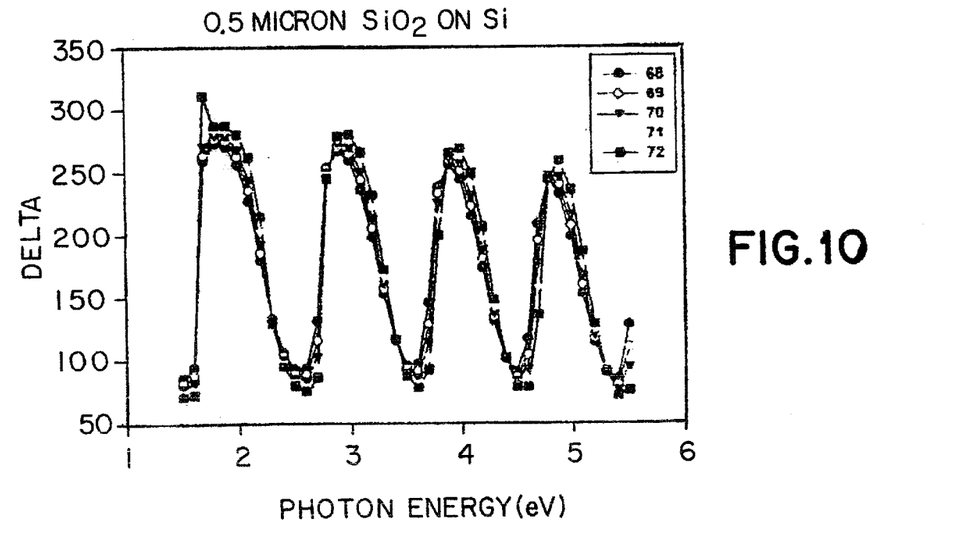
FIG. 10 is a plot at angles of incidence from 68 to 72 degrees, and, FIG. 11 is a plot of the difference between the averaged results of FIG. 10 and for a 70 degree angle of incidence.
Figure 11:
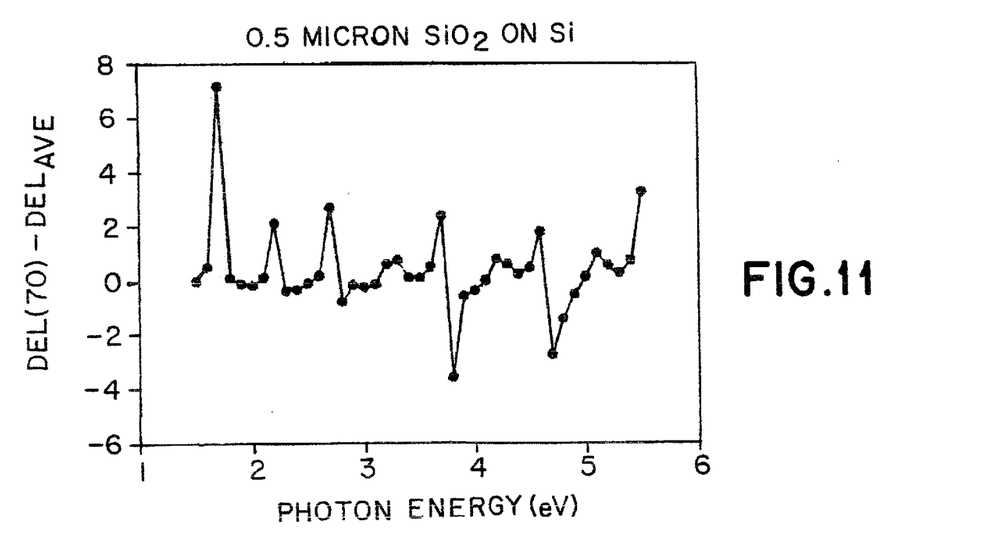

Still further, in practicing the invention the effect of the phenomenon called the Brewster's angle may be encountered. The Brewster's angle is a function of the wavelength and at that angle the parameter Delta ($\Delta$)=180 degrees. At this angle the sensitivity to angular errors is greatly enhanced and reflections of p-polarized light go to 0. Thus an initial alignment that is suitable for most of the spectrum may be inadequate for data close to the Brewster's angle. In accordance with the invention a solution to the problem is to modify the data analysis so as to reduce the weight that would be accorded to data where Delta (Δ) was close to 180 degrees. The situation is illustrated in connection with FIGS. 10 and 11. In FIG. 10 a plot of Delta versus photon energy of a 0.5 micrometer SiO on Si sample is shown for angles of incidence from 68 to 72 degrees, illustrating that in some but not all instances where Delta extrapolates to 180 degrees data glitches occur. In accordance with the invention if the points in the data where the average is not close to the results at the initial set up angle are eliminated in the analysis, the problem is eliminated. Referring to FIG. 11 a plot is shown of averaged Delta (Δ) versus Photon energy of a 0.5 micrometer SiO and Si sample at an initial setting of a 70 degree angle of incidence. In FIG. 11 the points to be eliminated from the average become readily apparent. What has been described is the capability of increasing the accuracy of the assigned value of the angle of incidence in ellipsometry metrology by averaging the measured values taken at two locations carrying + and − signs in the metrology analysis.

What is claimed is:

1. In mechanical-optical metrology apparatus of the type wherein polarized light is reflected from the surface of a sample that is under study and changes in said polarized light produced by characteristics in said surface of said sample under study are identified and quantified by analysis involving at least one mathmatical relationship that is dependent upon the angle of incidence of said polarized light with respect to the sample normal in said reflection from said surface of said sample, the improvement comprising:
establishing a value for said angle of incidence that is an average of positive and negative values of said angle of incidence for different arrangements of said mechanical-optical metrology apparatus.

2. The improvement of claim 1 wherein said average value is established through variations in at least one of direction of said light, and rotation of said sample.

3. Ellipsometry apparatus requiring an accurate angle of incidence with respect to a sample normal comprising: an incident light path serially including; an incident light source providing a beam, a polarizer, said incident beam striking a surface of a sample under study at a first angle and emanating in a reflection light beam at a second angle from the surface of said sample under study, and a sensing capability for changes in said light beam that are imparted in said reflection from said surface of said sample; and analysis means including establishing a value for said first angle that is an average of positive and negative values of said first angle, each of said positive and said negative values being the result of measuring with a different arrangement of said ellipsometry apparatus.

4. The ellipsometry apparatus of claim 3 wherein said different arrangement of said ellipsometry apparatus involves reversal of direction of said light in said light path.

5. The ellipsometry apparatus of claim 4 wherein said reversal of direction of said light beam includes: said first and said second angles being equal, a selectable separate light source positioned in, and said sensing capability being removable, in said reflection light path and a removable second sensing capability in said incident light path.

6. The ellipsometry apparatus of claim 3 wherein said different arrangement of said ellipsometry apparatus involves a separate light path for said reflection at a second angle from the surface of said sample under study.

7. The ellipsometry apparatus of claim 6 wherein said different arrangement of said ellipsometry apparatus includes a separate selectable reflection light path with a sensing capability.

8. The ellipsometry apparatus of claim 3 wherein said different arrangement of said ellipsometry apparatus invlves rotation of said sample under study.

9. The ellipsometry apparatus of claim 8 wherein said different arrangement of said ellipsometry apparatus involves rotation of said sample under study around a perpendicular axis of said sample and measuring a first angle of incidence averagable value where the normal of said sample is nearer said sensing capability in said reflection path, rotating said sample around said perpendicular axis and measuring a second angle of incidence averagable value where said normal of said sample is nearer said incident light source, and averaging said first and said second averagable values.

10. The method of establishing a value for the angle of incidence with respect to a sample normal in a mechanical-optical metrology apparatus of the type having an incident light path serially including; an incident light source providing a beam, a polarizer, said incident beam striking a surface of a sample under study at a first angle and emanating in a reflection light beam at a second angle from the surface of said sample under study, and a sensing capability for changes in said light beam that are imparted in said reflection from said surface of said sample, comprising the steps of:

measuring a first averagable value for said first angle,
changing the relationship between the mechanical and the optical components in said apparatus, producing thereby positive and negative values for said first angle,
measuring a second averagable value for said second angle, and
averaging said first and said second averagable values.

11. The method of claim 10 wherein said changing the relationship step involves rotating said sample 180 degrees about an axis that is close to the sample normal.

12. The method of claim 10 wherein said changing the relationship step involves reversing the direction of said light in said light path.

* * * * *